US012245887B2

(12) United States Patent
Xu et al.

(10) Patent No.: US 12,245,887 B2
(45) Date of Patent: Mar. 11, 2025

(54) ULTRASOUND SYSTEM FOR DETECTING LUNG CONSOLIDATION

(71) Applicant: KONINKLIJKE PHILIPS N.V., Eindhoven (NL)

(72) Inventors: Jingping Xu, Shanghai (CN); Balasundar Iyyavu Raju, North Andover, MA (US); Anthony M. Gades, Snohomish, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1079 days.

(21) Appl. No.: 16/960,647

(22) PCT Filed: Dec. 28, 2018

(86) PCT No.: PCT/EP2018/097057
§ 371 (c)(1),
(2) Date: Jul. 8, 2020

(87) PCT Pub. No.: WO2019/137817
PCT Pub. Date: Jul. 18, 2019

(65) Prior Publication Data
US 2020/0359991 A1    Nov. 19, 2020

(30) Foreign Application Priority Data

Jan. 10, 2018   (WO) ................. PCT/CN2018/072069
Feb. 27, 2018   (EP) ..................................... 18158739

(51) Int. Cl.
*A61B 8/08*    (2006.01)
*A61B 8/00*    (2006.01)
(Continued)

(52) U.S. Cl.
CPC ................. *A61B 8/085* (2013.01); *A61B 8/14* (2013.01); *A61B 8/463* (2013.01); *A61B 8/469* (2013.01);
(Continued)

(58) Field of Classification Search
CPC ........... A61B 8/085; A61B 8/14; A61B 8/463; A61B 8/469; A61B 8/5223; G16H 15/00;
(Continued)

(56) References Cited

U.S. PATENT DOCUMENTS 6,579,238 B1 *   6/2003   Simopoulos ........ G01S 15/8988
                                            600/443
9,277,877 B2     3/2016   Burlina et al.
(Continued)

FOREIGN PATENT DOCUMENTS

WO   2006044996 A2   4/2006
WO   2016046140 A1   3/2016

OTHER PUBLICATIONS

Rode, et al., "Positive end-expiratory pressure lung recruitment: comparison between lower inflection point and ultrasound assessment", Wiener Klinische Wochenschrift, The Middle European Journal of Medicine, Springler-Verlag, vol. 124, No. 23-24, Dec. 11, 2012, pp. 842-847.
(Continued)

*Primary Examiner* — John D Li

(57) ABSTRACT

The present disclosure describes ultrasound imaging systems and methods configured to identify lung abnormalities by determining a uniformity characteristic of a region of interest within ultrasound image frames. Systems can include an ultrasound transducer configured to acquire echoes responsive to ultrasound pulses transmitted toward a pulmonary target region. A processor coupled with the transducer may be configured to generate an image frame
(Continued)

from the acquired echoes and determine a uniformity characteristic of the region of interest below a pleural line in the image frame. The processor may also be configured to determine a presence or absence of a lung abnormality, e.g., lung consolidation, within the region of interest based on a value of the uniformity characteristic. If a lung abnormality has been determined to be present, the processor can generate an indicator of the same, which may be displayed on a user interface in communication with the processor.

17 Claims, 10 Drawing Sheets

(51) Int. Cl.
*A61B 8/14* (2006.01)
*G06T 7/00* (2017.01)
*G16H 15/00* (2018.01)
*G16H 30/40* (2018.01)
*G16H 50/20* (2018.01)
*G16H 50/30* (2018.01)

(52) U.S. Cl.
CPC .......... *A61B 8/5223* (2013.01); *G06T 7/0012* (2013.01); *G16H 15/00* (2018.01); *G16H 30/40* (2018.01); *G16H 50/20* (2018.01); *G16H 50/30* (2018.01); *G06T 2207/10132* (2013.01); *G06T 2207/30061* (2013.01)

(58) Field of Classification Search
CPC ........ G16H 50/30; G16H 50/20; G16H 30/40; G06T 7/0012; G06T 2207/10132
See application file for complete search history.

(56) References Cited

U.S. PATENT DOCUMENTS

| | | | |
|---|---|---|---|
| 2013/0089248 A1* | 4/2013 | Remiszewski | G06V 20/698 |
| | | | 382/128 |
| 2015/0002538 A1 | 1/2015 | Sohn et al. | |
| 2015/0150503 A1 | 6/2015 | Pamnani et al. | |
| 2016/0239959 A1* | 8/2016 | Blackbourne | G06V 10/40 |
| 2017/0091914 A1 | 3/2017 | Halmann et al. | |

OTHER PUBLICATIONS

Barrientos, et al., "Automatic detection of pneumonia analyzing ultrasound digital images", 2016 IEEE 36th Central American and Panama Convention, Nov. 9, 2016, pp. 1-4.
International Search Report and Written Opinion for International Application No. PCT/EP2018/097057, filed Dec. 28, 2018, 19 pages.
European Search Report for European Application No. EP18158739, dated Sep. 7, 2018, 3 pages.
Lim, et al., "Transthoracic Ultrasound Elastography in Pulmonary Lesions and Diseases", Ultrasound in Med. & Biol., 2017, vol. 43, No. 1, pp. 145-152.
Copetti, et al., Chest sonography: a useful tool to differentiate acute cardiogenic pulmonary edema from acute Cardiovascular Ultrasound 2008, Apr. 29, 2008, 6:16, pp. 1-10.
Wang, et al., "Lung ultrasound: a promising tool to monitor ventilator-associated pneumonia in critically ill patients", Critical Care, 2016, 20:320, pp. 1-10.
Corradi, et al., "Quantitative Analysis of Lung Ultrasonography for the Detection of Community-Acquired Pneumonia: A Pilot Study", Hindawi Publishing Corporation, BioMed Research International, vol. 2015, Article ID 868707, 8 pages.
G. Volpicelli, "Lung Sonograpy", J Ultrasound Med 2013; 32:165-171.
Tsai, et al., "Lung ultrasound imaging in avian influenza A (H7N9) respiratory failure", Critical Ultrasound Journal 2014, 6:6, 7 pages.

* cited by examiner

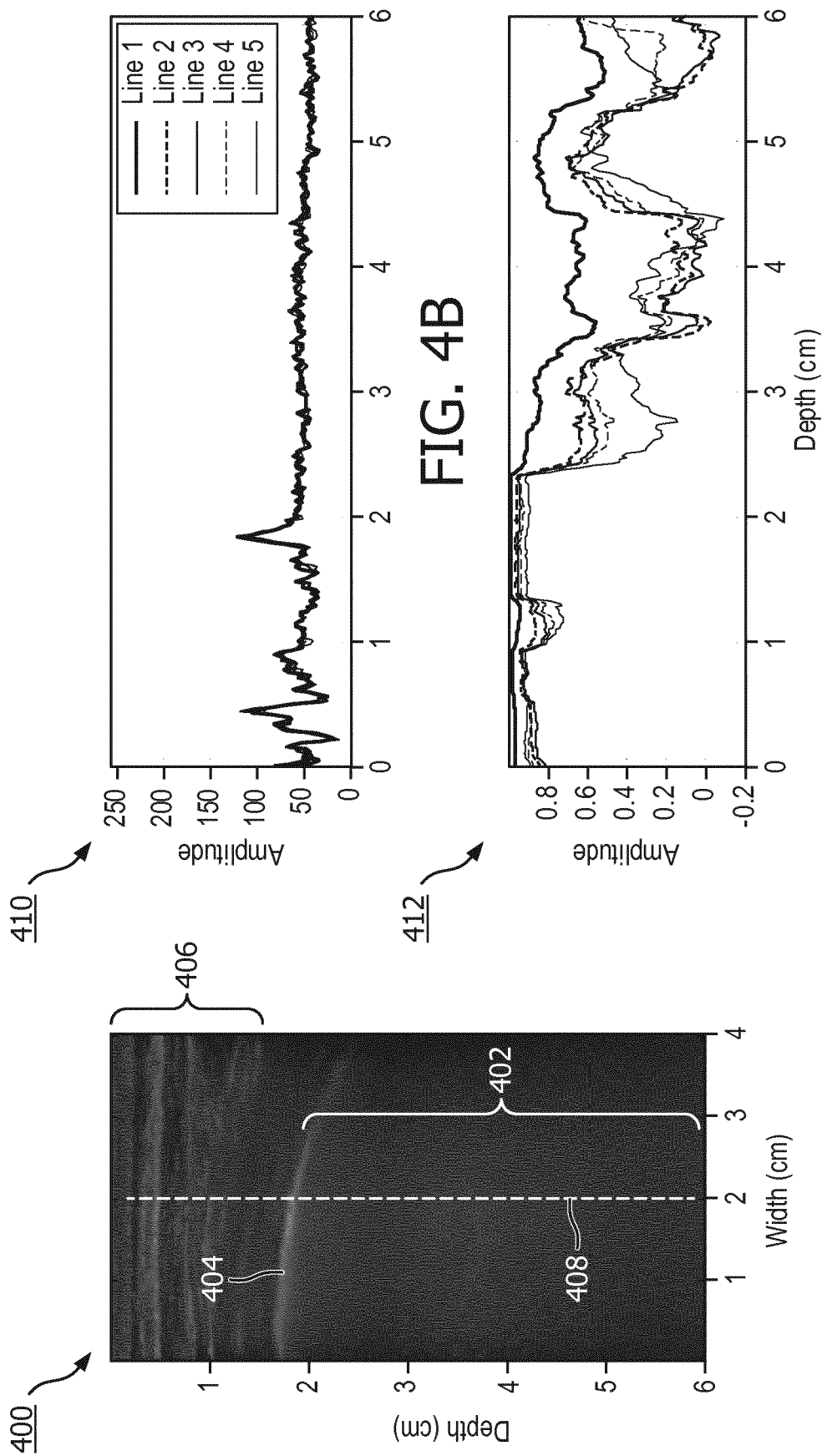

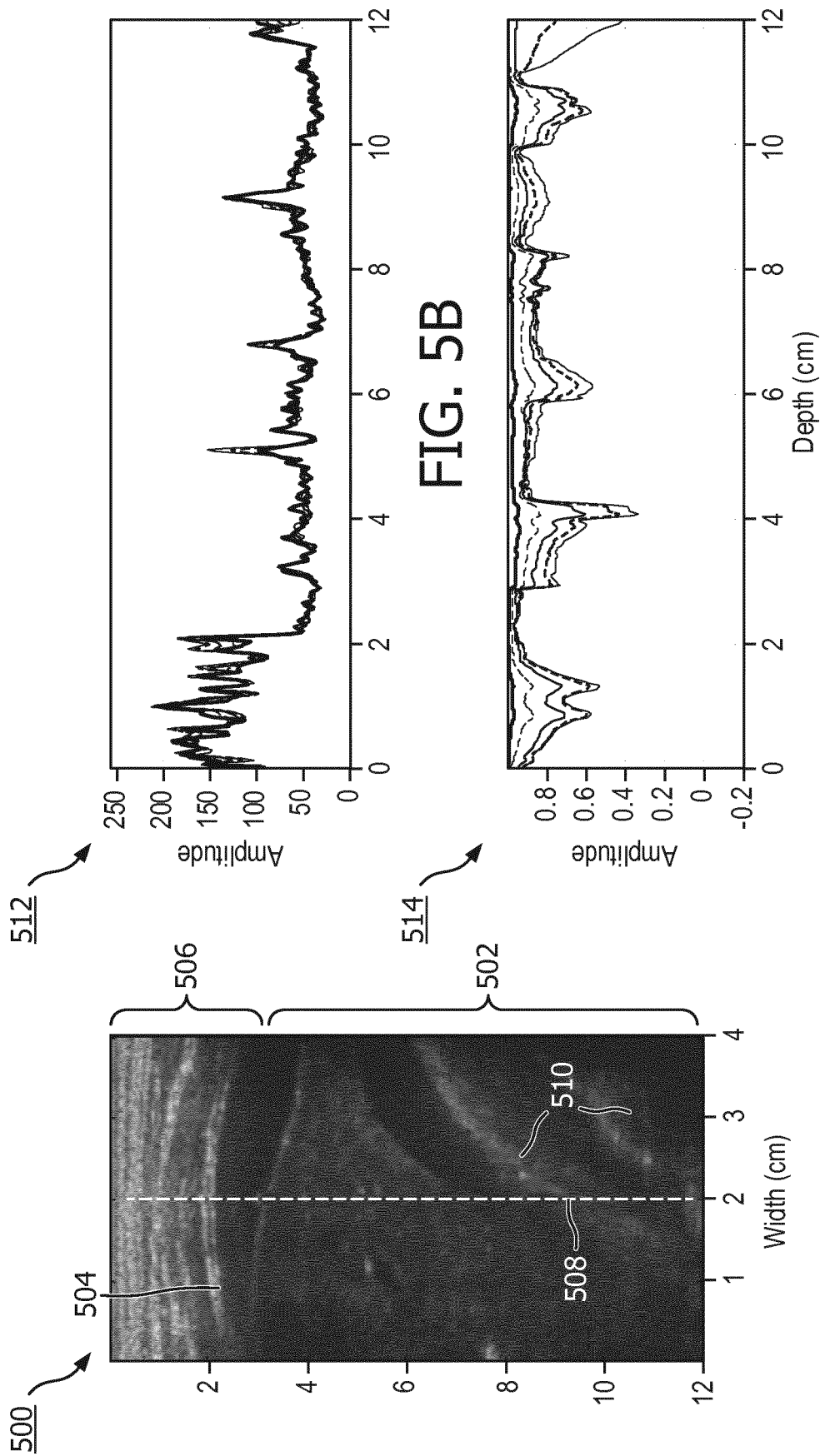

ULTRASOUND SYSTEM FOR DETECTING LUNG CONSOLIDATION

RELATED APPLICATIONS

This application is the U.S. National Phase application under 35 U.S.C. § 371 of International Application No. PCT/EP2018/097057, filed on Dec. 28, 2018, which claims priority to European Application Serial No. 18158739.5, filed Feb. 27, 2018, and International Application No. PCT/CN2018/072069, filed Jan. 10, 2018. These applications are hereby incorporated by reference herein.

TECHNICAL FIELD

The present disclosure pertains to automated ultrasound systems and methods for identifying lung abnormalities, such as lung consolidations.

BACKGROUND

A lung consolidation is a normally compressible region of lung tissue that has filled with fluid instead of gas. The presence of lung consolidation provides a common indication of many lung diseases and abnormalities, including pneumonia, lung cancer, atelectasis, acute respiratory distress syndrome, and acute lung injury. Accordingly, early diagnosis of such conditions typically depends on reliable detection of lung consolidation. Preexisting techniques for identifying lung consolidation include chest radiography (CXR) and thoracic CT imaging; however, both techniques are hampered by limited effectiveness. For example, CXR is only effective for identifying intermediate and/or large lesions or consolidations (for e.g., 1 cm), and thoracic CT imaging is typically unavailable at the point-of-care, e.g., bedside examination. In addition, radiation levels and high cost are often associated with both CXR and CT imaging. Other techniques, e.g., visual ultrasonography, may require a high level of operator expertise and effectiveness may depend on the presence of at least one hyperechoic feature within a pulmonary lesion, thereby rendering it vulnerable to low sensitivity unless the monitored lung condition has advanced at least to an intermediate stage. Ultrasound-based diagnoses may also vary greatly based on operator subjectivity and experience. New technology for identifying lung consolidations is therefore needed to improve the ease and accuracy of diagnosing numerous pulmonary conditions.

US 2016/239959 A1 provides a method for identifying internal trauma in a patient for pneumothorax, hemothorax, and abdomincal hemorrahge using features extracted from B-mode and M-mode ultraound images, including A-lines, B-lines from B-mode images and barcode, sky, seashore, beach patterns from M-mode images.

SUMMARY

The present disclosure describes automated, ultrasound-based systems and methods for detecting and characterizing lung abnormalities, including lung consolidations. For ease of description, lung consolidation detection will be described herein, although it is understood that other abnormalities may also be detected according to the methods disclosed. Such abnormalities may include various lesions, pleural effusions, material buildup, abnormal growths or masses, tumors, fluid accumulation, etc. In embodiments, abnormalities detectable via systems herein may exclude pneumothorax due to the location and characteristics of pneumothorax, which necessitate distinct means of detection. Particular implementations involve systems configured to identify lung abnormalities during an ultrasound scan by interrogating a region of interest below the pleural line and determining a uniformity characteristic of the ultrasound image frames obtained therefrom. In various embodiments, systems can include an ultrasound transducer configured to transmit beams of ultrasonic energy toward a region of interest that includes at least a portion of a lung, and receive ultrasonic echoes responsive to the beams. A processor, e.g., a signal processor, coupled with the transducer can generate image frames from the echoes. The term "image frame" used herinwith, unless specified otherwise, refers to an image composed of a plurality of pixels, each of which plurality of pixels corresponds to a different spatial point in the region of interest, or in otherwords, refers to an image which represents a snapshot of the region of interest. For example, the image frame can be any kind of B-mode image, including but not limited to fundmental B-mode image, harmonic B-mode image, etc. Hence, the image frame is not an M-mode ultrasound image. As well-known, the M-mode is defined as time motion display of the ultrasound wave along a chosen ultrasound scan line. Typically, each lateral line of an M-mode image represents the temporal changes in echoes reflected by a same spatial point. Via the same or a different processor, the system can proceed to automatically identify the pleural line within the image frames and define a region of interest below, i.e., extending to a greater anatomical depth than, the pleural line, where lung consolidations frequently appear. The processor can also determine intensity levels of the pixels comprising the image frames within the region of interest. Using the determined intensity levels, the processor can determine a uniformity characteristic embodying variation in the intensity levels within the region of interest. The variation can be determined, expressed and processed in various ways. For example, the processor can be configured to calculate an average intensity level within the region of interest, which can be used by the processor to determine a standard deviation from the average. In additional examples, the processor can be configured to generate spatial correlation maps of the region of interest by performing intensity comparisons between laterally spaced image pixels. Because increased variation in image intensity may be associated with a greater likelihood of the presence of lung consolidation, the processor can be configured to confirm the presence or absence of lung consolidations based on the degree of variation. Determining the extent of variation may be accomplished by applying a threshold value to the uniformity characteristic, for instance. Systems can also include a user interface, which may feature a display screen configured to receive various user inputs and display an indicator of the presence or absence of lung consolidation during an ultrasound scan. The indicator can take several forms, e.g., visual and/or audio cues, provided that it is configured to communicate the presence of a lung consolidation to the operator of the system.

In accordance with some examples, an ultrasound imaging system may include an ultrasound transducer configured to acquire echoes responsive to ultrasound pulses transmitted toward a target region comprising a lung. The system may further include a processor in communication with the ultrasound transducer. The processor may be configured to generate an image frame from the echoes; determine a uniformity characteristic of a region of interest below a pleural line in the image frame; determine a presence or absence of a lung abnormality within the region of interest based on a value of the uniformity characteristic; generate an indicator if a lung abnormality has been determined to be present; and display the indicator on a user interface in communication with the processor.

In some examples, the processor may be configured to quantify the uniformity characteristic in the form of a spatial correlation and/or de-correlation map of image intensity. In some embodiments, the processor may be configured to determine the spatial correlation and/or de-correlation map by comparing image intensity values of pairs of individual pixels within the image frame, the pairs laterally separated by a defined interval of pixels. In some implementations, the processor may be configured to adjust the defined interval of pixels in response to a user input received at the user interface. In some examples, the uniformity characteristic may comprise a standard deviation from an average image intensity. In some embodiments, the uniformity characteristic may comprise a total speckle size and/or local spatial speckle size within the region of interest.

In some implementations, the lung abnormality may be lung consolidation. According to such implementations, the processor may be further configured to apply a threshold value to the uniformity characteristic, wherein the presence of a lung consolidation is confirmed if the value of the uniformity characteristic exceeds the threshold value. In some examples, the user interface may be further configured to display a number of lung abnormalities present within the region of interest, a location of the lung abnormality, a type of the lung abnormality, a variation in lung abnormality volume, or combinations thereof. In some embodiments, the user interface may be configured to generate and display an ultrasound image during an ultrasound scan. The indicator may comprise, in some examples, a graphic overlay superimposed on the lung abnormality within the ultrasound image. In some implementations, the user interface may be further configured to guide a user through an ultrasound scan of the target region of a patient by providing an instruction for orienting the ultrasound transducer. In some embodiments, the processor may be further configured to determine a scan distance to the lung abnormality during an ultrasound scan. In some examples, the instruction may be based on a previously conducted ultrasound scan of the patient and stored in a memory coupled with the processor.

A method in accordance with the present disclosure may involve acquiring echo signals responsive to ultrasound pulses transmitted into a target region by a transducer operatively coupled to an ultrasound system; generating an image frame from the ultrasound echoes; determining a uniformity characteristic of a region of interest below a pleural line in the image frame; determining a presence or absence of a lung abnormality within the region of interest based on a value of the uniformity characteristic; generating an indicator if a lung abnormality has been determined to be present; and displaying the indicator on a user interface in communication with the processor.

In some examples, the method may further involve quantifying the uniformity characteristic in the form of a spatial correlation map of image intensity. In some embodiments, quantifying the uniformity characteristic in the form of a spatial correlation map may comprise comparing image intensity values of pairs of individual pixels within the image frame, the pairs laterally separated by a defined interval of pixels. In some implementations, determining the uniformity characteristic may comprise determining a standard deviation from an average image intensity. In some implementations, determining the uniformity characteristic may comprise determining a total speckle size and/or local spatial speckle size within the region of interest. In some examples, the lung abnormality may include lung consolidation. According to such examples, the method may further involve applying a threshold value to the uniformity characteristic. The presence of a lung consolidation may be confirmed if the value of the uniformity characteristic exceeds the threshold value.

In some embodiments, the method may further involve generating a report comprising a number of lung abnormalities present within the region of interest, a location of the lung abnormality, a type of the lung abnormality, a variation in lung abnormality volume, or combinations thereof. In some implementations, the method may further involve guiding a user through an ultrasound scan of the target region of a patient by providing an instruction for orienting the ultrasound transducer. In some examples, the method may further involve determining a scan distance to the lung abnormality during an ultrasound scan.

Any of the methods described herein, or steps thereof, may be embodied in non-transitory computer-readable medium comprising executable instructions, which when executed may cause a processor of a medical imaging system to perform the method or steps embodied herein. For example, a non-transitory computer-readable medium comprising executable instructions may, when executed, cause a processor of an ultrasound system to: receive an image frame, the image frame being generated from ultrasound echo data acquired from a target region comprising a lung; determine a uniformity characteristic of a region of interest below a pleural line in the image frame; determine a presence or absence of a lung abnormality within the region of interest based on a value of the uniformity characteristic; and generate an indicator if a lung abnormality has been determined to be present. In accordance with some examples, an apparatus for detecting lung abnormality on the basis of ultrasound echo data may include a data interface. The data interface may be configured to receive an image frame, the image frame being generated from ultrasound echo data acquired from a target region comprising a lung. The data interface may also be configured to output an indicator if a lung abnormality has been determined to be present. The apparatus may also include a processor configured to determine a uniformity characteristic of a region of interest below a pleural line in the image frame; determine a presence or absence of a lung abnormality within the region of interest based on a value of the uniformity characteristic; and generate the indicator if a lung abnormality has been determined to be present.

BRIEF DESCRIPTION OF THE DRAWINGS

FIG. 4A is an ultrasound image of a normal lung, showing a pleural line and an area of spatial randomness beneath the pleural line.

FIG. 4B is a graph of image amplitude as a function of anatomical depth detected along a plurality of laterally spaced, single-pixel lines, corresponding to the image of FIG. 4A.

FIG. 4C is a graph of spatial correlation as a function of anatomical depth, corresponding to the graph of FIG. 4B.

FIG. 5A is an ultrasound image of an abnormal lung, showing a pleural line and an area containing lung consolidations beneath the pleural line.

FIG. 5B is a graph of image amplitude as a function of anatomical depth detected along a plurality of laterally spaced, single-pixel lines, corresponding to the image of 5A.

FIG. 5C is a graph of spatial correlation as a function of anatomical depth, corresponding to the graph of FIG. 5B.

DETAILED DESCRIPTION

Figure 1:
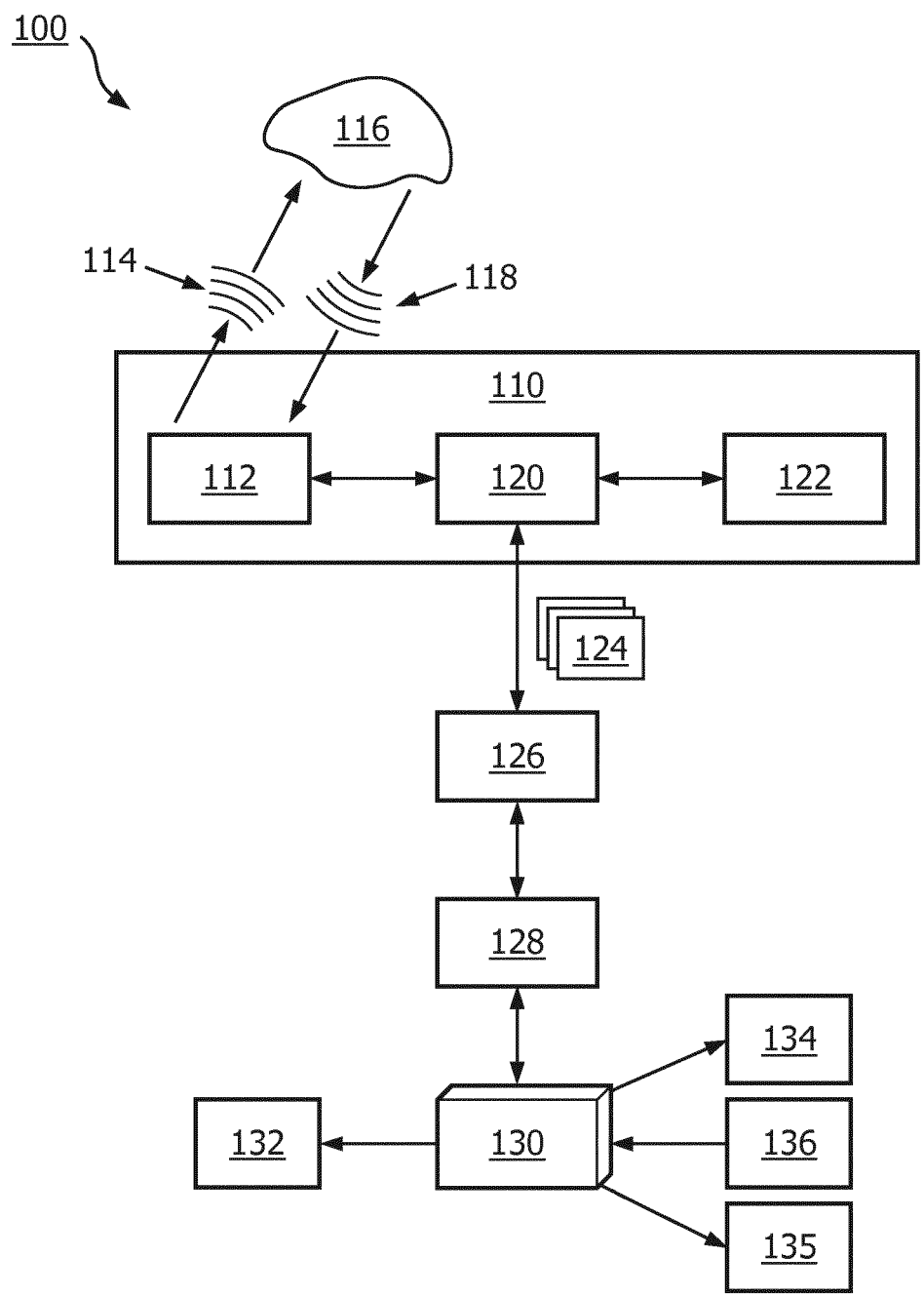
FIG. 1 is a block diagram of an ultrasound system in accordance with principles of the present disclosure.

The following description of certain embodiments is merely exemplary in nature and is in no way intended to limit the invention or its applications or uses. In the following detailed description of embodiments of the present systems and methods, reference is made to the accompanying drawings which form a part hereof, and which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

The present technology is also described below with reference to block diagrams and/or flowchart illustrations of methods, apparatus (systems) and/or computer program products according to the present embodiments. It is understood that blocks of the block diagrams and/or flowchart illustrations, and combinations of blocks in the block diagrams and/or flowchart illustrations, may be implemented by computer executable instructions. These computer executable instructions may be provided to a processor, controller or controlling unit of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

As provided herein, ultrasound-based interrogation of a pulmonary region of interest coupled with automated analysis of acquired ultrasound image frames can increase the sensitivity of lung consolidation detection while decreasing the level of operator expertise required for such detection. Ultrasound signatures of lung consolidations may resemble soft tissue signatures or soft tissue mixed with air signatures, which the systems herein may be configured to identify. Particular embodiments can include ultrasound systems configured to determine at least one uniformity characteristic indicative of lung consolidation beneath the pleural line within ultrasound image frames of a lung. In specific examples, the uniformity characteristic can comprise a standard deviation from an average image intensity level determined through the region of interest. In addition or alternatively, the uniformity characteristic can comprise a spatial correlation map of the region beneath the pleural line. According to such examples, systems may be configured to identify lung consolidations where spatial correlation is high (and spatial de-correlation is low), and confirm the absence of lung consolidations where spatial correlation is low (and spatial de-correlation is high). The relationship between the uniformity characteristic and the presence of lung consolidations has been discovered via ultrasound-based interrogation of various pulmonary regions, and subsequent comparisons of the brightness values of pixels within the acquired ultrasound image frames. Equipped with acoustic properties specific to normal lung tissue and abnormal lung tissue, systems herein are configured to distinguish normal lungs from abnormal lungs in automated fashion. By identifying lung consolidations in automated fashion, i.e., without subjective user interpretation, systems herein may reduce examination times, especially for inexperienced ultrasound operators, and provide standardized methods for evaluating ultrasound signatures for the presence or absence of lung abnormalities. Results generated according to the systems and methods described can be displayed visually, e.g., in real time during an ultrasound scan, thereby providing the information necessary to guide an operator through an ultrasound scan. Over time, repeated ultrasound scanning performed according to the methods disclosed may be used to monitor treatment progress in patients with a range of lung conditions. Various ultrasound modalities may be implemented according to the systems disclosed herein. For example, an ultrasound transducer may be configured to perform B-mode imaging, such that a processor coupled with the transducer detects lung consolidation by determining spatial correlation properties of the grayscale values in the B-mode image frames. Embodiments may also generate and utilize radiofrequency or channel data to detect lung consolidations and generate spatial correlation maps of a region of interest. In addition or alternatively, an ultrasound transducer may also be configured detect lung consolidation via tissue harmonic imaging. The systems and methods described herein can be employed to diagnose and monitor numerous pulmonary conditions. For example, the detection and characterization of lung consolidations may be used, either by the system or a user, to diagnose conditions such as pneumonia, lung cancer, atelectasis, acute respiratory distress syndrome, and acute lung injury.

FIG. 1 shows an example ultrasound system 100 configured to determine the presence or absence of a pulmonary abnormality, e.g., lung consolidation, in accordance with the present disclosure. As shown, the system 100 can include an ultrasound data acquisition unit 110, which may include an ultrasound probe containing an ultrasound sensor array 112 configured to transmit ultrasound signals or beams 114 into a target region 116, which can include one or both lungs within a patient. Ultrasound echo signals 118 responsive to the transmitted beams are received by the acquisition unit 110, which may also include a beamformer 120 coupled to the ultrasound transducer array 112, along with a signal processor 122, which may be configured to generate a plurality of discrete ultrasound image frames 124 from the ultrasound echoes 118 received at the array 112. The system may also include a data processor 126, e.g., a computational module or circuitry, configured to analyze the image frames 124, e.g., by determining intensity levels of the image pixels constituting the frames, determining uniformity properties within the image frames, and applying a threshold to the determined uniformity properties. In some embodiments, the system also includes a display processor 128 coupled with the data processor 126 and a user interface 130. The display processor 128 can be configured to generate ultrasound images 132 from the image frames 124, an indicator 134 that conveys the presence or absence of lung consolidation within one or more of the image frames 124, and a report 135 containing information about the lung consolidations detected. The user interface 130 (or data interface) can be configured to display the ultrasound images 132 in real time as an ultrasound scan is being performed. The indicator 134 may be displayed or communicated concurrently to provide real-time updates to the operator of the system 100 that one or more lung consolidations may be present. The user interface 130 can also be configured to receive a user input 136 at any time before, during, or after an ultrasound scan. In some examples, the user interface 130 can receive image frames 124 directly from the data acquisition unit 110. The configuration of the system 100 shown in FIG. 1 may vary. For example, the system 100 can be portable or stationary. In some embodiments, the system may comprise a processor of an ultrasound system, which can be a non-imaging system, e.g., an analysis workstation, configured for post-acquisition analysis of ultrasound data in the particular manner described herein. Various portable devices, e.g., laptops, tablets, smart phones, or the like, may be used to implement one or more functions of the system 100. In examples that incorporate such devices, the ultrasound sensor array 112 may be connectable via a USB interface, for example.

The ultrasound data acquisition unit 110 may be configured to acquire ultrasound echoes 118 from one or more target regions 116, which can include one or more lungs or sub-regions thereof. The ultrasound sensor array 112 may include at least one transducer array configured to transmit and receive ultrasonic energy. A variety of transducer arrays may be used, e.g., linear arrays, convex arrays, or phased arrays. The number and arrangement of transducer elements included in the sensor array 112 may vary in different examples. For instance, the ultrasound sensor array 112 may include a 1D or 2D array of transducer elements, corresponding to linear array and matrix array probes, respectively. The 2D matrix arrays may be configured to scan electronically in both the elevational and azimuth dimensions (via phased array beamforming) for 2D or 3D imaging.

A variety of users having a range of skill levels may handle and operate the ultrasound data acquisition unit 110. Due to the automated processing performed by the system 100, users having minimal experience operating ultrasound equipment may effectively acquire ultrasound image frames 124 that confirm whether the lung region being scanned includes a lung consolidation, even if the consolidation is relatively small and the associated lung condition has not advanced beyond an early stage. To conduct a scan in accordance with the methods described herein, especially for determining the area or volume of lung consolidations, transverse scanning may be employed with optional longitudinal scanning employed when necessary.

As further shown in FIG. 1, the data acquisition unit 110 can include a beamformer 120, which may control the transmission of ultrasonic energy, for example by forming ultrasonic pulses into focused beams. The beamformer 120 may control the width of the transmitted ultrasound beams. In some examples, a series of ultrasound scans may be performed over a region of interest, and the beamformer 120 can be configured to adjust the beam width in each successive scan. The beamformer 120 can adjust the beam width automatically, e.g., in accordance with an automated program, or in response to user input. The beamformer 120 may also be configured to control the reception of ultrasound signals such that discernable image data may be produced and processed with the aid of other system components. The role of the beamformer 120 may vary in different ultrasound probe varieties. In some embodiments, the beamformer 120 may comprise two separate beamformers: a transmit beamformer configured to receive and process pulsed sequences of ultrasonic energy for transmission into a subject, and a separate receive beamformer configured to amplify, delay, and/or sum received ultrasound echo signals. In some embodiments, the beamformer 120 may comprise a microbeamformer operating on groups of sensor elements for both transmit and receive beamforming, coupled to a main beamformer which operates on the group inputs and outputs for both transmit and receive beamforming, respectively.

The signal processor 122 may be communicatively, operatively, and/or physically coupled with the sensor array 112 and/or the beamformer 120. In the example shown in FIG. 1, the signal processor 122 is included as an integral component of the data acquisition unit 110, but in other examples, the signal processor 122 may be a separate component. The signal processor 122 may be configured to receive unfiltered and disorganized ultrasound data embodying the ultrasound echoes 118 received at the sensor array 112. From this data, the signal processor 122 may continuously generate a plurality of ultrasound image frames 124 as a user scans the region 116.

One or more additional processors, such as data processor 126, can also be included. The data processor 126, communicatively coupled with the data acquisition unit 110, may perform one or more operations in addition to or in lieu of one or more operations performed by the signal processor 122. The data processor 126 is uniquely configured to receive and analyze the ultrasound image frames 124 for the presence of one or more lung consolidations. After determining whether a lung consolidation is shown within the image frames 124, the data processor 126 may communicate an indication of the determined presence or absence of lung consolidation to the graphics processor 128 or directly to the user interface 130.

The display processor 128 communicatively coupled with the data processor 126 may be configured to generate an indicator 134 based on the determination made by the data processor 126. The indicator 134 may indicate the presence or absence of at least one lung consolidation within the image frames 124. Upon receiving the ultrasound images 132 and/or the indicator 134, the user interface 130 may then display the images and/or the indicator. The indicator 134 may be displayed concurrently with, e.g., superimposed on top of or next to, the ultrasound images 132 in real time as the images are obtained. Accordingly, the indicator 134 may notify the user of the presence or absence of one or more lung consolidations. In some examples, the indicator 134 may comprise a sensory cue that is not be visibly displayed, such as a vibration of the ultrasound probe or an audible cue emitted from speakers coupled with the ultrasound system 100. The indicator 134 may also comprise a light that turns on and off or changes color. For example, the presence of a lung consolidation may be indicated by a green light, while the absence of an lung consolidation may be indicated by a red light or an absence of light. In some embodiments, the indicator 134 may be displayed without the concurrent display of ultrasound images. The particular nature of the indicator 134 is not critical, provided the indicator is configured to notify the user of the presence or absence of lung consolidations.

In some embodiments, the indicator 134 may also include information about the lung consolidation(s) detected. For example, during an ultrasound scan, the indicator 134 may display the depth of a lung consolidation beneath the pleural line or the scan distance to the lung consolidation. In addition, the indicator 134 may provide the cross-sectional area and/or volume of a particular lung consolidation. This information, like the depth, may be overlaid on a live ultrasound image, such that the user can determine the dimensions of any detected lung consolidations as the scan is being performed. This information may be stored in a memory for later reference.

In some embodiments, the user interface 130 may also be configured to guide or assist a user through an ultrasound scan. Such guidance may be responsive to the indicator 134 generated by the display processor 128. For example, the user interface 130 may provide a first instruction to the user in response to receiving an indicator 134 conveying the presence of a lung consolidation, and in response to receiving an indicator 134 conveying the absence of a lung consolidation, may provide a second, distinct instruction to the user. Such instructions may prompt the user to perform the ultrasound scan in a particular manner that ensures all lung abnormalities, especially consolidations, if present, are detected during a given scan. Instructions may include directional commands, e.g., "Orient probe transversely with respect to chest region"; or "Move probe laterally." Instructions may also include technique-based commands, e.g., "Move ultrasound probe slower"; "Slow down"; "Stop"; "or "Continue." In some examples, the instructions may guide the user to position the ultrasound probe in a particular manner before initiating the ultrasound scan, such that the probe transmits ultrasound beams into the most common areas of lung consolidation formation. These initial instructions may be different for different lung conditions. For example, the recommended initial probe position and/or orientation may different for detecting lung consolidations associated with pneumonia versus atelectasis.

Figure 2:
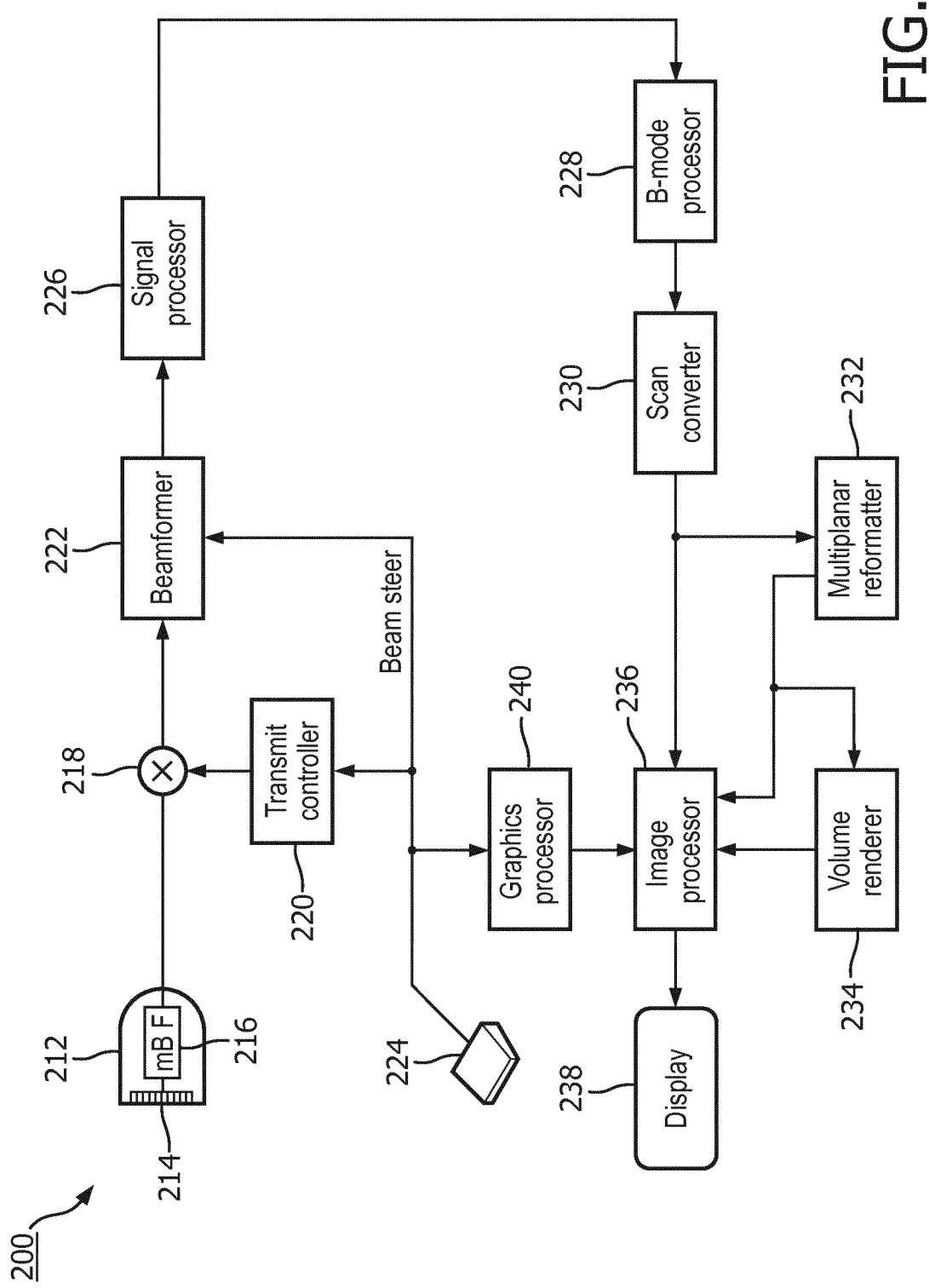
FIG. 2 is a block diagram of another ultrasound system in accordance with principles of the present disclosure.

FIG. 2 is a block diagram of another ultrasound system 200 in accordance with principles of the present inventions. One or more components shown in FIG. 2 may be included within a system configured to detect lung consolidations within a pulmonary region of a subject, provide an indication of the same, and guide a user operating the system through an ultrasound scan in search of lung consolidations. For instance, any of the above-described functions of the signal processor 122, data processor 126, and/or display processor 128 may be implemented and/or controlled by one or more of the processing components shown in FIG. 2, including for example, signal processor 226, B-mode processor 228, scan converter 230, multiplanar reformatter 232, volume renderer 234, graphics processor 240, and/or image processor 236.

In the ultrasonic imaging system of FIG. 2, an ultrasound probe 212 includes a transducer array 214 for transmitting ultrasonic waves into a pulmonary region and receiving echo information responsive to the transmitted waves. In various embodiments, the transducer array 214 may be a matrix array or a one-dimensional linear array. The transducer array 214 may be coupled to a microbeamformer 216 in the probe 212 which may control the transmission and reception of signals by the transducer elements in the array. In the example shown, the microbeamformer 216 is coupled by the probe cable to a transmit/receive (T/R) switch 218, which switches between transmission and reception and protects the main beamformer 222 from high energy transmit signals. In some embodiments, the T/R switch 218 and other elements in the system can be included in the transducer probe rather than in a separate ultrasound system component. The transmission of ultrasonic beams from the transducer array 214 under control of the microbeamformer 216 may be directed by the transmit controller 220 coupled to the T/R switch 218 and the beamformer 222, which receives input, e.g., from the user's operation of the user interface or control panel 224. A function that may be controlled by the transmit controller 220 is the direction in which beams are steered. Beams may be steered straight ahead from (orthogonal to) the transducer array, or at different angles for a wider field of view. The partially beamformed signals produced by the microbeamformer 216 are coupled to a main beamformer 222 where partially beamformed signals from individual patches of transducer elements are combined into a fully beamformed signal.

The beamformed signals may be communicated to a signal processor 226. The signal processor 226 may process the received echo signals in various ways, such as bandpass filtering, decimation, I and Q component separation, and/or harmonic signal separation. The signal processor 226 may also perform additional signal enhancement via speckle reduction, signal compounding, and/or noise elimination. In some examples, data generated by the different processing techniques employed by the signal processor 226 may be used by a data processor to detect one or more lung consolidations. The processed signals may be coupled to a B-mode processor 228, which may employ amplitude detection. The signals produced by the B-mode processor 228 may be coupled to a scan converter 230 and a multiplanar reformatter 232. The scan converter 230 may arrange the echo signals in the spatial relationship from which they were received in a desired image format. For instance, the scan converter 230 may arrange the echo signals into a two dimensional (2D) sector-shaped format. The multiplanar reformatter 232 may convert echoes which are received from points in a common plane in a volumetric region of the body into an ultrasonic image of that plane, as described in U.S. Pat. No. 6,443,896 (Detmer). In some examples, a volume renderer 234 may convert the echo signals of a 3D data set into a projected 3D image as viewed from a given reference point, e.g., as described in U.S. Pat. No. 6,530,885 (Entrekin et al.). The 2D or 3D images may be communicated from the scan converter 230, multiplanar reformatter 232, and volume renderer 234 to an image processor 236 for further enhancement, buffering and/or temporary storage for display on an image display 237. Prior or after their display, one or more indicators may be overlaid or superimposed on the images to highlight or label areas of lung consolidation. A graphics processor 240 can generate the graphic overlays for display with the ultrasound images. The graphic overlays may contain, e.g., standard identifying information such as patient name, date and time of the image, imaging parameters, and the like, and also various outputs generated by one or more additional processors included within the system, such as one or more indicators conveying the presence or absence of lung consolidations. In some examples, the indicator may be provided by a display (e.g., a side-by-side display of quantification of one or more parameters alongside the ultrasound image), such as by displaying a spatial correlation map or a map generated based on a uniformity characteristic associated with the image or portion thereof. Graphic overlays may also include visual instructions, e.g., text and/or symbols, for guiding a user of the system 200 through an ultrasound scan. In some examples, the graphics processor may receive input from the user interface 224, such as a typed patient name or confirmation that an instruction displayed or emitted from the interface has been acknowledged by the user of the system 200. The user interface 224 may also receive input prompting adjustments in the settings and/or parameters used by the system 200, input requesting additional instructions or assistance for performing an ultrasound scan, and/or input requesting that one or more ultrasound images be saved and/or transmitted to a remote receiver. The user interface may also be coupled to the multiplanar reformatter 232 for selection and control of a display of multiple multiplanar reformatted (MPR) images.

Figure 3B:
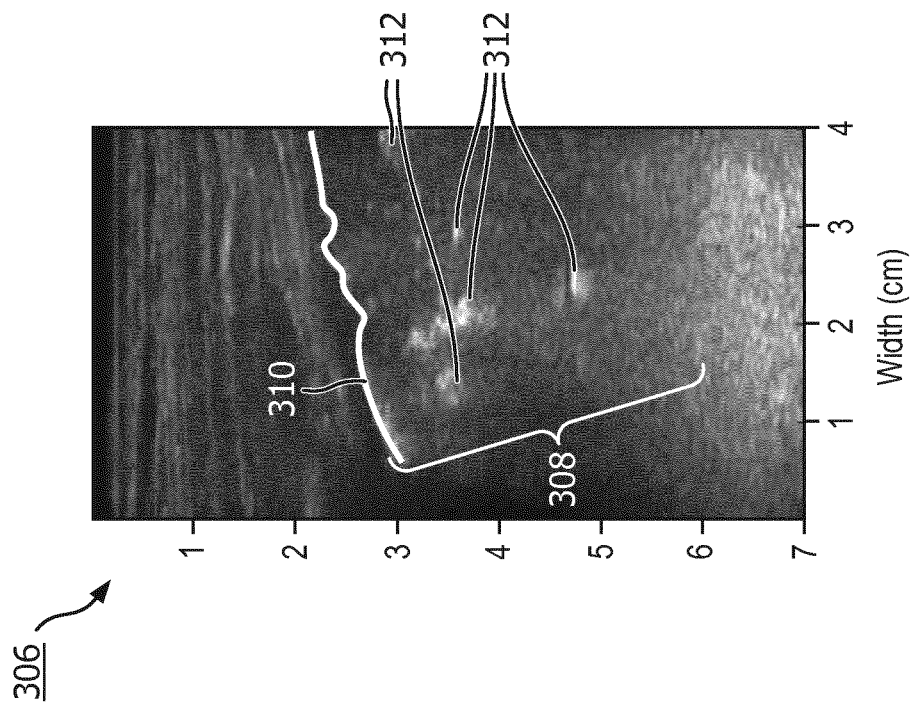
FIG. 3B is an ultrasound image of an abnormal lung harboring multiple lung consolidations within a region of interest beneath a pleural line.
Figure 3A:
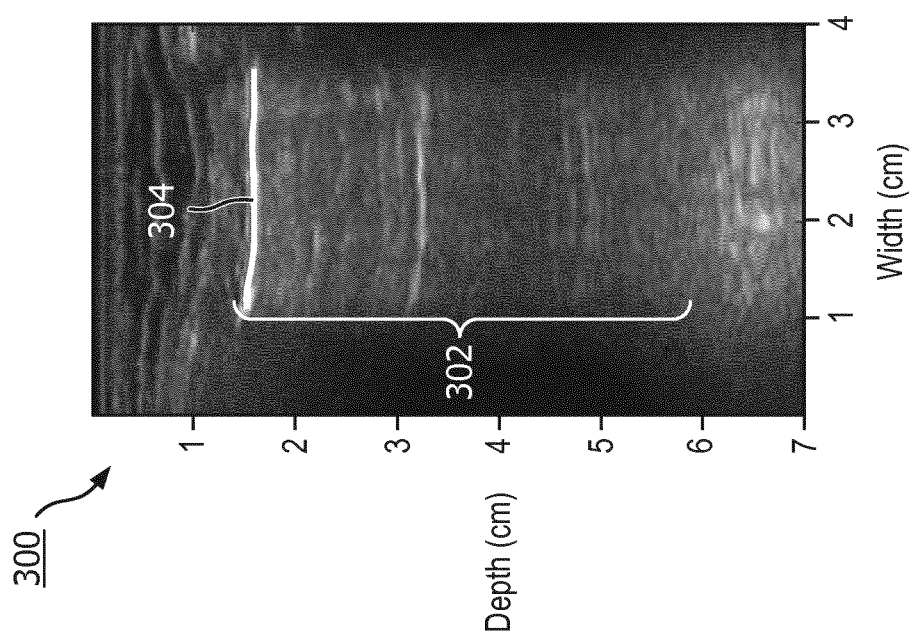
FIG. 3A is an ultrasound image of a normal lung, showing a region of interest beneath a pleural line.

FIG. 3A is an ultrasound image 300 of a normal lung acquired via the systems disclosed herein, showing a region of interest 302 beneath a pleural line 304, which appears as an echogenic line marking the interface between the patient's chest wall and the lung. In the absence of lung consolidation, the region of interest 302 may be predominantly characterized by spatial randomness without any distinct hyper- or hypoechoic regions indicative of tissue, bone and/or or fluid. Systems disclosed herein, e.g., system 100 and/or 200, can be configured to automatically identify the pleural line 304 within at least one image frame via one or more processors, such as data processor 126. In some embodiments, systems can be configured to pinpoint the pleural line by identifying and processing A-line artefacts that may appear upon imaging the pleural interface, for example as described in PCT/EP2017/082054 (Balasundar), which is incorporated by reference in its entirety herein. For example, systems herein may be configured to identify candidate pleural lines and A-lines within acquired image frames, compute the intensity of at least one of the A-lines, and apply the computed A-line intensity to indicate a target placement of an ultrasound probe for imaging the pleural interface. A user interface herein may be configured to alert the user that a target placement of the ultrasound probe has been obtained once the pleural line appears within an image frame. In specific embodiments, a processor disclosed herein can be configured to apply a threshold value to the computed A-line intensity, and if the A-line intensity exceeds the threshold value, the processor may determine that the pleural line has been identified via the proper probe position and orientation. Accordingly, one or more A-line artefacts may also appear in the region of interest 302, against a backdrop of spatial randomness. In additional embodiments, a user may identify a pleural line upon visual examination of a live ultrasound image displayed on the user interface.

Systems according to the present disclosure can be configured to define the region of interest 302 in automated fashion, or with additional user input. For example, systems according to the present disclosure can be configured to extract a region of interest from one or more image frames by identifying a pleural line and then trimming the image frame(s) to satisfy pre-specified, sub-pleural dimensions. By reducing the area of each image frame that is processed, the processing capacity may be reduced and the processing speed enhanced. The region of interest 302 may extend downward from the pleural line 304, away from the surface of the patient. Accordingly, the pleural line can provide an anatomical landmark utilized by the system to determine various consolidation statistics, such as depth, location, and size variations. The depth of the region of interest 302 may span the distance necessary to capture sub-pleural consolidations, which are typically located immediately beneath the pleural line, and deep lung consolidations, which are located deeper beneath the pleural line. In some examples, the user may input a desired depth of the region of interest, for example if the user's objective is to examine a particular, known consolidation. In some embodiments, e.g., for examining deep lung consolidations, the user may specify a maximum depth for the region of interest. In some examples, the region of interest may be systematically defined using patient-specific data, which may be input into the system prior to initiation of the ultrasound scan, or the region of interest may have a consistent depth which is systematically defined based on historical medical data.

FIG. 3B is an ultrasound image 306 of an abnormal lung acquired via an example system disclosed herein, showing a region of interest 308 beneath a pleural line 310. As shown, a plurality of lung consolidations 312, visible as distinct, spot-like hyperechoic regions, are visible within the region of interest 308. Lung consolidations such as those shown in FIG. 3B may appear in patients harboring air bronchograms, which are air-filled bronchi. In additional examples, one or more reverberation artefacts, e.g., vertical B-lines, may also appear within the region of interest 308, for instance at an early stage of various pulmonary diseases. Fluid bronchograms may also be produced as a result of lung consolidation, which may appear as one or more hypoechoic regions in an ultrasound image.

To identify the lung consolidations 312 visible within the ultrasound image 306 shown in FIG. 3B, a processor, e.g., processor 126, can be configured to determine at least one uniformity characteristic embodied by the image. Quantifiable differences between the uniformity characteristic of the region of interest 302 shown in FIG. 3A and the region of interest 308 shown in FIG. 3B can then be utilized to confirm the presence or absence of lung consolidations. In particular embodiments, systems may be configured to identify the uniformity characteristic by determining intensity amplitudes for individual pixels via analysis of each pixel within the image frames acquired by an ultrasound transducer. Intensity amplitudes may be determined by one or more processors, such as the signal processor 122 and/or data processor 126 shown in FIG. 1. Using the intensity amplitudes, the processor(s) may proceed to determine the average amplitude of the pixels throughout the region of interest, along with the standard deviation therefrom. The determinations made by the processor(s) may be expressed as a function of depth beneath the pleural line or one or more additional anatomical features.

As shown in FIG. 3B, the lung consolidations 312 have a substantially higher and consistent amplitude than the background area comprising the region of interest 308. By contrast, the region of interest 302 shown in FIG. 3A lacks similar high-amplitude regions. As a result, the standard deviation from the average amplitude may be greater for the region of interest 308 shown in FIG. 3B compared to the standard deviation of the region of interest 302 shown in FIG. 3A. Greater standard deviations resulting from the echogenic consolidations 312 can be utilized by systems herein to confirm that the region of interest 308 includes at least one lung consolidation. In some examples, systems may be configured to apply a threshold to distinguish regions of interest lacking any consolidation, e.g., region of interest 302, from regions of interest containing at least one consolidation, e.g., region of interest 308. The threshold applied by the system may be based on accumulated medical data, which may be patient-specific in some embodiments. For example, such data may provide the minimum standard deviation that is consistently indicative of lung consolidation, or the minimum standard deviation that indicates a clinically relevant risk of lung consolidation presence. Standard deviations above this threshold value may be indicative of the presence of lung consolidation, and standard deviations below this threshold value may be indicative of the absence of lung consolidation.

In some embodiments, systems may be configured to detect the speckle size present within the ultrasound image 306, based on the amplitudes of the pixels comprising the image. As determined with respect to standard deviation values, speckle size for a normal lung may be smaller than speckle size for a lung harboring one or more consolidations. Accordingly, systems contemplated herein can be configured to apply a threshold speckle size to a speckle size value extracted from a region of interest. Speckle sizes above the threshold may indicate the presence of lung consolidation, while speckle sizes below the threshold may indicate an absence of lung consolidation. Embodiments may involve determining local speckle size in both the lateral and axial direction.

In some examples, the presence or absence of lung consolidation within a region of interest, along with associated consolidation type(s) and spatial boundaries, may be determined via systems herein by generating spatial correlation or de-correlation maps of the region of interest. As shown in FIGS. 4 and 5 and described below, high spatial correlation within a region of interest may be indicative of lung consolidation, while low spatial correlation may be indicative of normal, consolidation-free lung tissue. By precisely determining the spatial correlation properties within processed ultrasound image frames, systems herein may improve the sensitivity of consolidation detection, especially for patients harboring only small to moderately sized consolidations, for which correlation properties may be difficult to discern.

FIG. 4A is an ultrasound image 400 of a normal lung, showing a region of interest 402 beneath a pleural line 404 and a portion of the chest wall 406. As shown, the region of interest 402 is devoid of any lung consolidations or any imaging artefacts. The majority of the area below the pleural line 404 thus lacks any distinct echogenic features. To determine the spatial correlation properties of the region of interest, systems can be configured to determine intensity amplitudes for individual pixels via analysis of each pixel within the image frames acquired by an ultrasound transducer. To determine the spatial correlation of such amplitudes, a processor can compare the amplitudes of laterally spaced pixel pairs. As an example, a processor can determine amplitude values along a one-pixel-wide reference line 408 that extends vertically through the region of interest 402 and above the pleural line 404, near the 2-cm mark in the particular example shown. The amplitude value at each pixel varies along the reference line 408 as it passes through various features visible within the image 400, ranging from relatively high values when passing through bright regions, and relatively low values when passing through dark regions. To determine the spatial correlation of the amplitude values within the region of interest 402, the pixelated amplitudes for various numbers of additional lines, e.g., five lines, each laterally spaced at a different interval with respect to the reference line 408, may also be selected and compared to the individual amplitudes of the reference line 408 as a function of anatomical depth. Based on the size of the lateral interval between the reference line 408 and each additional line, along with the amplitude values for each line, spatial correlation can be determined. In some examples, the chest wall, which may have relatively consistent acoustic properties, e.g., high intensity and high spatial correlation, can be used as a reference amplitude. In some embodiments, spatial correlation values may be stored and accumulated to refine consolidation thresholds based on a sample of patients.

In some examples, systems herein may be configured to determine spatial de-correlation properties and generate spatial maps accordingly. For example, reductions in spatial correlation across defined pixel intervals, e.g., two pixels, can be determined and quantified as a de-correlation value. According to such examples, spatial de-correlation may be higher for normal lung tissue and lower for consolidated lung tissue.

In additional embodiments, spatial correlation properties can be derived as a function of ultrasound transmittal changes, e.g., the width of the transmitted ultrasound beam. As beam width is adjusted, spatial correlation (or de-correlation) properties may vary in a distinct manner depending on whether normal or consolidated tissue is present. For example, for consolidated lung tissue, localized spatial correlation values may increase as the ultrasound beam width used to interrogate the tissue is also increased. By contrast, for normal tissue, localized spatial correlation values may remain relatively constant as beam width is increased. Detecting these distinctions regarding the extent of localized spatial correlation in consolidated versus normal tissue may involve performing multiple ultrasound scans, each scan performed using a transmittal beam of distinct width. Spatial correlation or de-correlation values determined for each scan can then be compared to determine and characterize the relationship between changing the beam width and the resulting spatial correlation or de-correlation values detected.

FIG. 4B is a graph 410 of image amplitude as a function of anatomical depth for each of five additional lines along which amplitude was measured in image 400. The lines are numbered in accordance with their distance from the reference line, i.e., line 1 is the closest and line 5 is the furthest. As shown, amplitude values remain relatively low from a depth of 0 cm to about 6 cm for each of the lines, regardless of their separation from the reference line 408. The amplitude peaks around the more shallow depths within the region of interest correspond to the echogenic features of the chest wall and pleural interface.

FIG. 4C is a graph 412 of spatial correlation as a function of anatomical depth. The spatial correlation depicted in the graph 412 is based on a comparison between each of the lines shown in FIG. 4B and the reference line 408. As shown, spatial correlation is high at the more shallow depths spanning about zero to about 2.2 cm, regardless of interval size, where the chest wall and pleural line produce similarly echogenic signatures. Beneath the pleural line, for example beginning at about 2.2 cm, the spatial correlation between each interval and the reference line 408 drops substantially. Within this sub-region, correlation values approach zero at several depths, where the image is characterized primarily by spatial randomness. Correlation values are especially low for lines more laterally separated from the reference line, e.g., line #5. Thus, amplitude values change substantially upon moving laterally away from the reference line at most depths below about 2.2 cm, where the image 400 lacks defined areas of brightness. Such spatial randomness may serve as an acoustic signature of consolidation-free regions of a lung being scanned. Accordingly, systems described herein may be configured to confirm that a region of interest lacks consolidations by detecting areas of similar spatial randomness.

FIG. 5A is an ultrasound image 500 of an abnormal lung, showing a region of interest 502 beneath a pleural line 504 and a portion of the patient's chest wall 506. Using a processor, a reference line 508 may be defined, which passes through multiple tissue-like consolidations 510 demarcated by similarly echogenic, tissue-like patterns. Due to the strong, tissue-like patterns appearing in the region of interest 502, the spatial correlation between the amplitude values of laterally separated image pixels may be moderate to high, which the processor can be configured to determine by calculating the amplitude correlations between multiple pairs of laterally separated pixels within the ultrasound image.

FIG. 5B is a graph 512 of image amplitude as a function of anatomical depth for each of the five additional lines for which amplitude was measured in image 500, each line laterally separated from the reference line by a different interval size. As in graph 410, the graph 512 of FIG. 5B shows amplitude spikes at shallow depths, where the chest wall and pleural line produce strong, echogenic signatures. Unlike the amplitude values shown in graph 410, however, the amplitude values shown in graph 512 spike repeatedly and nearly uniformly at greater depths beneath the pleural line, for example at depths of about 5, 7, 9 and 12 cm. Anatomical depths associated with low amplitude values, for example from about 2 cm to slightly less than 5 cm, are nearly uniformly low for each of the lines analyzed.

FIG. 5C is a graph 514 of spatial correlation as a function of anatomical depth. The spatial correlation depicted in the graph 514 is based on a comparison between each of the lines shown in FIG. 5B and the reference line 508 extending through the region of interest at about the 2 cm mark. As shown, spatial correlation between the reference line 508 and each of the variously spaced comparison lines is relatively high throughout the image depth spanning 0 cm to 12 cm. Reductions in spatial correlation, for example around 4 and 6 cm, correspond to sub-regions of greater spatial randomness, which lack defined areas of brightness. In contrast to the spatial correlation information generated from the image 400 shown in FIG. 4A, the spatial correlation of the region of interest 502 defined in FIG. 5A is relatively high, even upon moving laterally away from the reference line 508. Such spatial consistency may serve as an acoustic signature for one or more lung consolidations present within a lung being scanned. Accordingly, systems provided herein may be configured to confirm that a region of interest contains lung consolidation by detecting areas of similarly high spatial correlation.

Figure 6B:
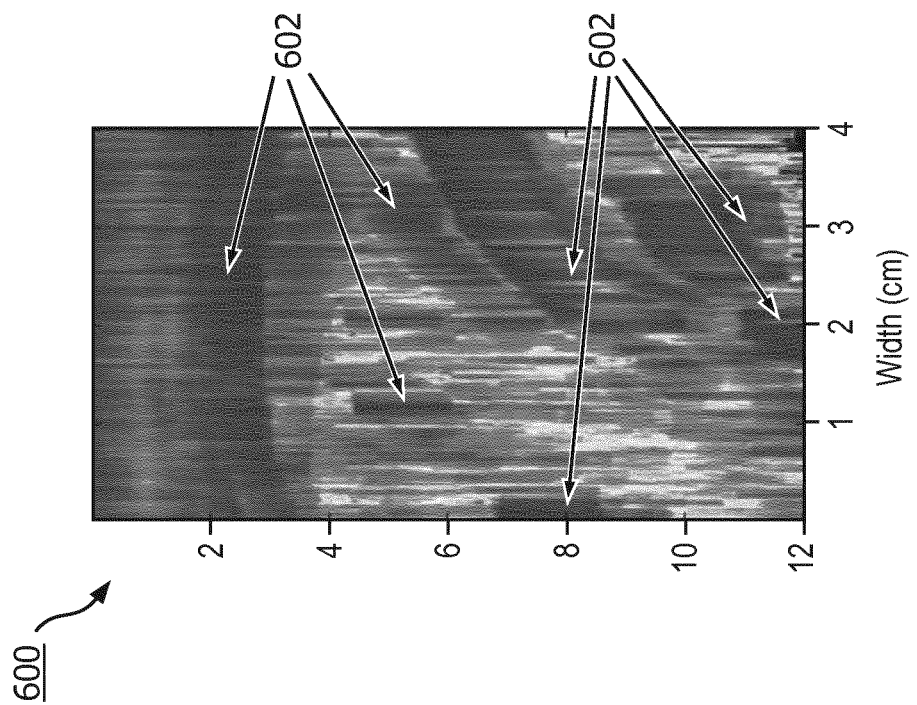
FIG. 6B is a spatial correlation map generated using the amplitudes detected in the ultrasound image of FIG. 5A.
Figure 6A:
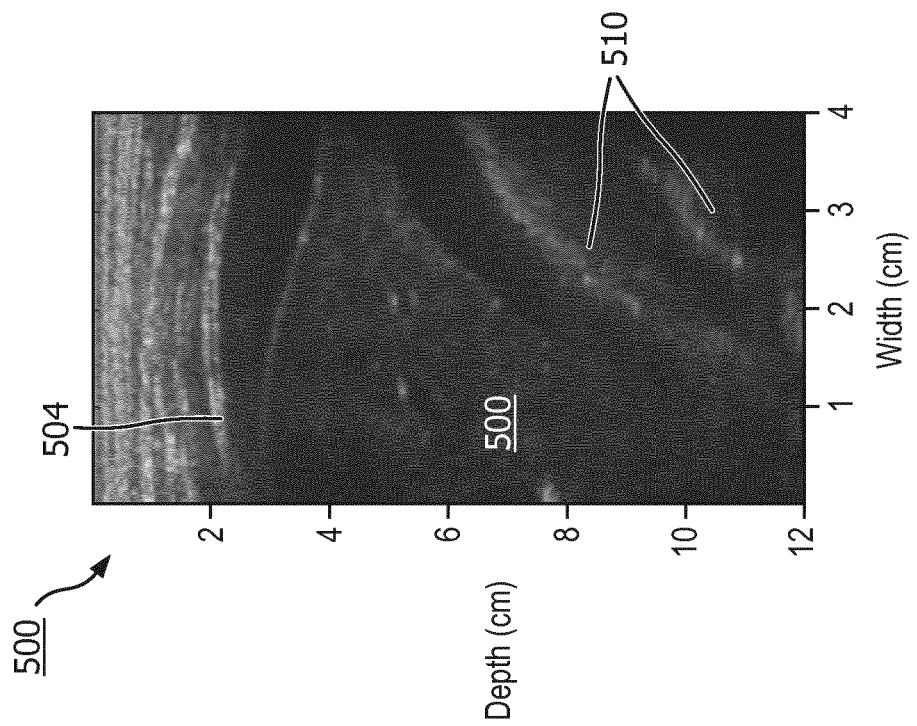
FIG. 6A is the ultrasound image of FIG. 5A.

For reference, FIG. 6A again shows the ultrasound image 500 of FIG. 5A. FIG. 6B is a spatial correlation map 600 generated using the amplitudes detected in image 500. To generate the map, a processor can be configured to perform spatial correlation analysis based on the image amplitudes of each pixel comprising the ultrasound image 400. In some embodiments, the system can be configured to determine spatial correlation values produced by a defined lateral interval of pixels, e.g., 1, 2, 4, 8, 16, 24 pixels, or any range therebetween. Using the defined lateral pixel interval, the processor can identify areas of high spatial correlation, low spatial correlation, and correlation values therebetween. Spatial de-correlation values can be determined analogously, for example by subtracting a determined spatial correlation coefficient from a value of 1. As shown in FIG. 6B, spatial correlation is high for the majority of the image pixels, particularly at the high areas 602 marked with arrows. The high spatial correlation is indicative of the presence of lung consolidations. In some examples, the lateral interval size may be adjusted by a user. Adjustments may be necessary to refine the spatial correlation determinations, for example, when detecting relatively small or faint lung consolidations.

Figure 7B:
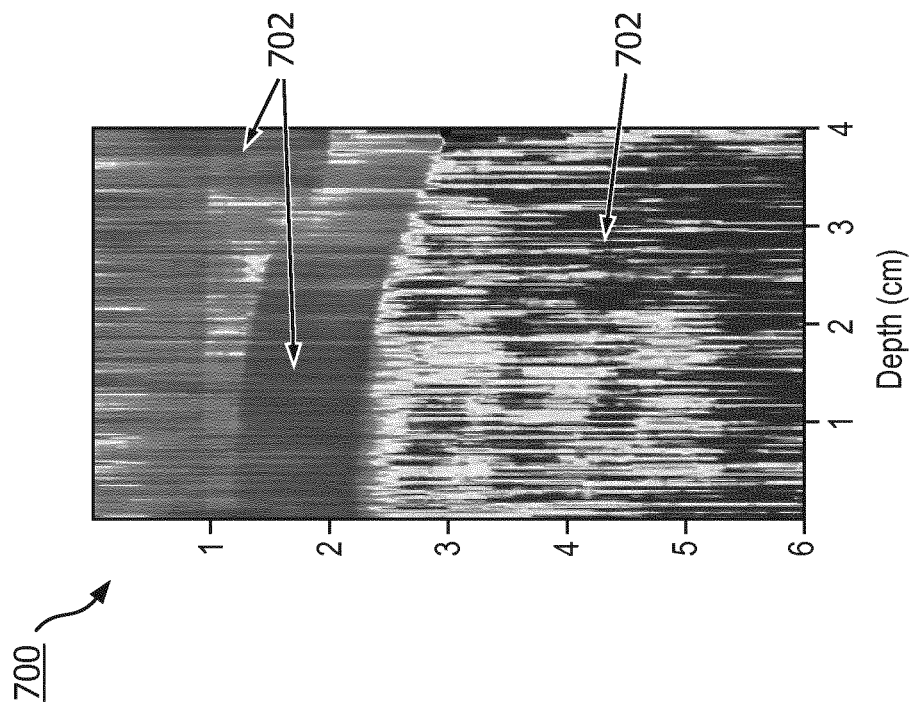
FIG. 7B is a spatial correlation map generated using the amplitudes detected in the ultrasound image of FIG. 7A.
Figure 7A:
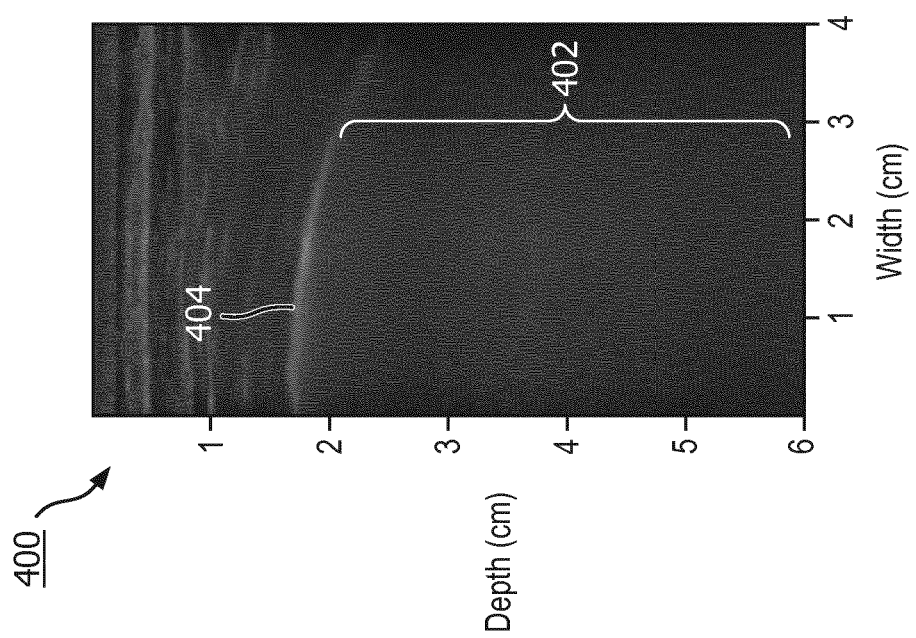
FIG. 7A is the ultrasound image of FIG. 4A.

FIG. 7A shows the ultrasound image 400 of FIG. 4A adjacent to the spatial correlation map 700 of FIG. 7B. In contrast to the spatial correlation map 600 shown in FIG. 6B, the spatial correlation map 700 includes distinct sub-regions of high spatial correlation 702 and low spatial correlation 704. The highly correlated sub-regions 702 encompass the chest wall and pleural line, while the sub-regions of low spatial correlation 704 encompass the area beneath the pleural line lacking any lung consolidations. As can be seen, there is a sharp drop in spatial correlation beneath the pleural line for the normal lung depicted in FIGS. 7A and 7B, and a small drop in spatial correlation beneath the pleural line for the consolidated lung shown in FIGS. 6A and 6B. The spatial correlation maps 600, 700 may be generated by one or more processors, e.g., data processor 126 and display processor 128, and displayed on a display screen or user interface. In some examples, the maps may be displayed during an ultrasound scan, adjacent to a live ultrasound image, or after an ultrasound scan has been completed.

In some examples, temporal correlation may also be determined via the systems described herein. The degree of reliance placed on temporal correlation to detect lung consolidation may vary. In some examples, temporal correlation may be implemented to supplement spatial correlation, such that spatial correlation determinations can be confirmed via temporal correlation. To successfully correlate tissue structure in a temporal manner, a moderate to high acquisition frame rate may be necessary; however, temporal correlation may be determined without a high frame rate if lung motion is slow, for example at the end of expiration or the peak of inspiration.

Figure 8:
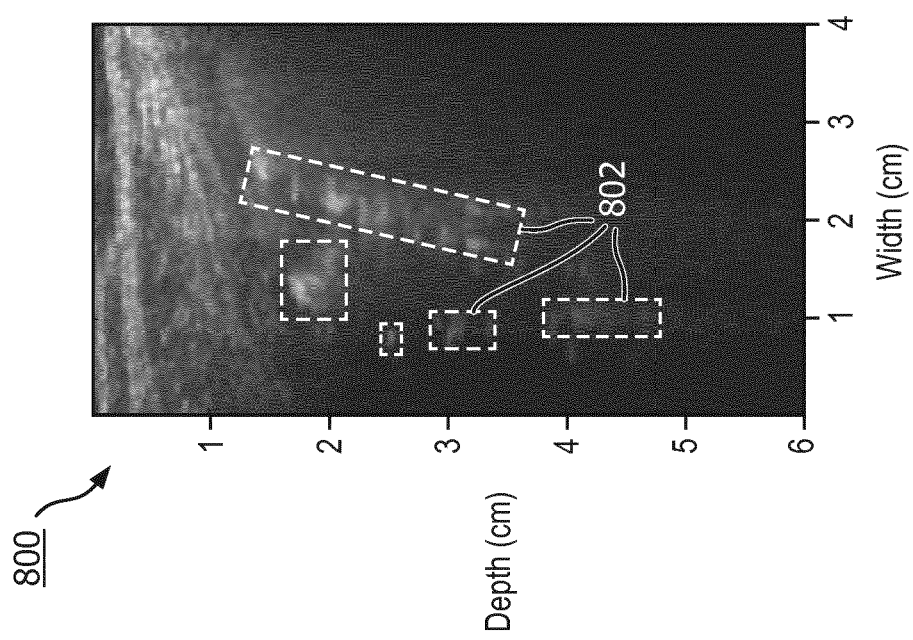
FIG. 8 is an ultrasound image comprising a plurality of graphic overlays demarcating regions of lung consolidation.

FIG. 8 is an ultrasound image 800 comprising a plurality of graphic overlays 802 demarcating regions of lung consolidation. The image 800 of FIG. 8 provides one example of an ultrasound image that may be displayed on a user interface or display screen. Areas of lung consolidation may be determined in real time during an ultrasound scan and labeled on the screen using graphic overlays 802. In other examples, the system may be configured to indicate the presence of lung consolidations in a different manner. For instance, the graphic overlays may be color coded, or no overlays may be included at all. In some examples, the graphic overlays may be superimposed on the spatial correlation map generated by the system. The overlays may be labeled and accompanied by various statistics determined by the system. For instance, each overlay may be accompanied by an indication of consolidation depth, cross-sectional area, volume and/or spatial coordinates. In additional examples, the overlays may be accompanied by a confidence level determined by the system. The confidence level may convey the likelihood that a given area within a region of interest corresponds to a lung consolidation. For instance, areas of very high spatial correlation, e.g., near 1.0, may be assigned a high confidence level, while areas of moderate spatial correlation, e.g., near 0.6, may be assigned at medium confidence level. Embodiments may include an icon displayed on the image when lung consolidation is detected.

After a lung ultrasound scan has been completed, systems herein may provide a summary report, e.g., report 135, comprising information determined during the scan, e.g., the number and/or size of the lung consolidations detected. The information included in the report may be generated by a processor, e.g., data processor 126. Reports may be generated to supplement or replace ultrasound images complete with graphic overlays. For example, reports may be produced and transmitted to a clinician for non-imaging applications of the present technology. In some examples, the type of consolidations detected, e.g., sub-pleural vs. deep, may also be included in the report. Example reports may also contain information regarding variation in lung consolidation determined over time. For instance, a report may contain information regarding a change in the volume of one or more consolidations relative to a previously determined volume. Such information may be indicative of the effectiveness of a particular treatment regimen. For example, reductions in lung consolidation volume may indicate that an applied treatment is effective. In some examples, systems may be configured to determine the proportion of an intercostal space comprised of lung consolidation.

Figure 9:
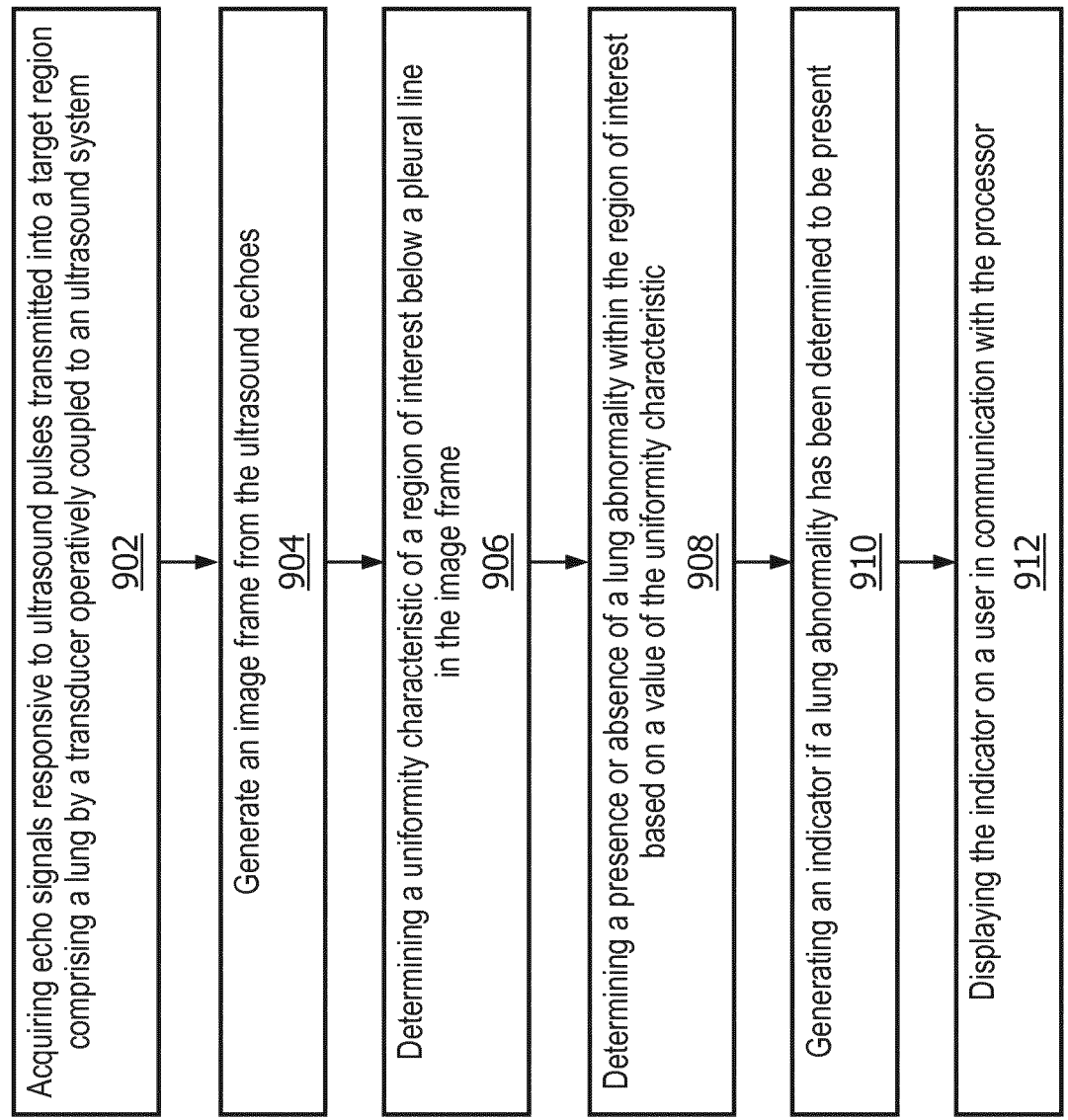
FIG. 9 is a method performed in accordance with principles of the present disclosure.

FIG. 9 is a block diagram of an ultrasound imaging method in accordance with the principles of the present disclosure. The example method 900 of FIG. 9 shows the steps that may be utilized, in any sequence, by the systems and/or apparatuses described herein for identifying lung consolidations during an ultrasound scan, which may be performed by a novice user via instructions or live ultrasound images annotated with lung consolidation information provided during an ultrasound scan. The method 900 may be performed by an ultrasound imaging system, such as system 100, or other systems including, for example, a mobile system such as LUMIFY by Koninklijke Philips N. V. ("Philips"). Additional example systems may include SPARQ and/or EPIQ, also produced by Philips.

In the embodiment shown, the method 900 begins at block 902 by "acquiring echo signals responsive to ultrasound pulses transmitted into a target region comprising a lung by a transducer operatively coupled to an ultrasound system." In some embodiments, the ultrasound transducer may be operated by a user lacking extensive ultrasound experience.

At block 904, the method involves "generating an image frame from the ultrasound echoes." The image frame may be generated using one or more processors, which may be included with the transducer in a data acquisition unit. In some examples, discrete signal processors and data processors may be utilized for generating the image frame. A plurality of image frames may be generated at variable frame rates.

At block 906, the method involves "determining a uniformity characteristic of a region of interest below a pleural line in the image frame." The specific uniformity characteristic may vary. In some examples, the uniformity characteristic may be quantified in the form of a spatial correlation map of image intensity. Quantifying the characteristic in the form of a spatial correlation may involve comparing image intensity values of pairs of individual pixels within the image frame. The pixel pairs can be laterally spaced by a defined interval of pixels, which may be adjustable by a user in some embodiments. In some embodiments, determining the uniformity characteristic may involve determining a standard deviation from an average image intensity.

At block 908, the method involves "determining a presence or absence of a lung abnormality within the region of interest based on a value of the uniformity characteristic." In various implementations, the lung abnormality is lung consolidation, which may be sub-pleural consolidation and/or deep consolidation. According to such examples, the method 900 may further involve applying a threshold value to the uniformity characteristic, where the presence of a lung consolidation is confirmed if the value of the uniformity characteristic exceeds the threshold value.

At block 910, the method involves "generating an indicator if a lung abnormality has been determined to be present." The indicator may take multiple forms, and may be binary, e.g., off/on, or it may change gradually to convey a range of information.

At block 912, the method involves "displaying the indicator on a user interface in communication with the processor." Embodiments may further involve generating a report that includes information about the lung abnormalities detected. Specific information may include, in some examples, a number of lung abnormalities present within the region of interest, a location of the lung abnormality, a type of the lung abnormality, a variation in lung abnormality volume, or combinations thereof. Examples may further involve determining a scan distance to the lung abnormality during an ultrasound scan.

Figure 10:
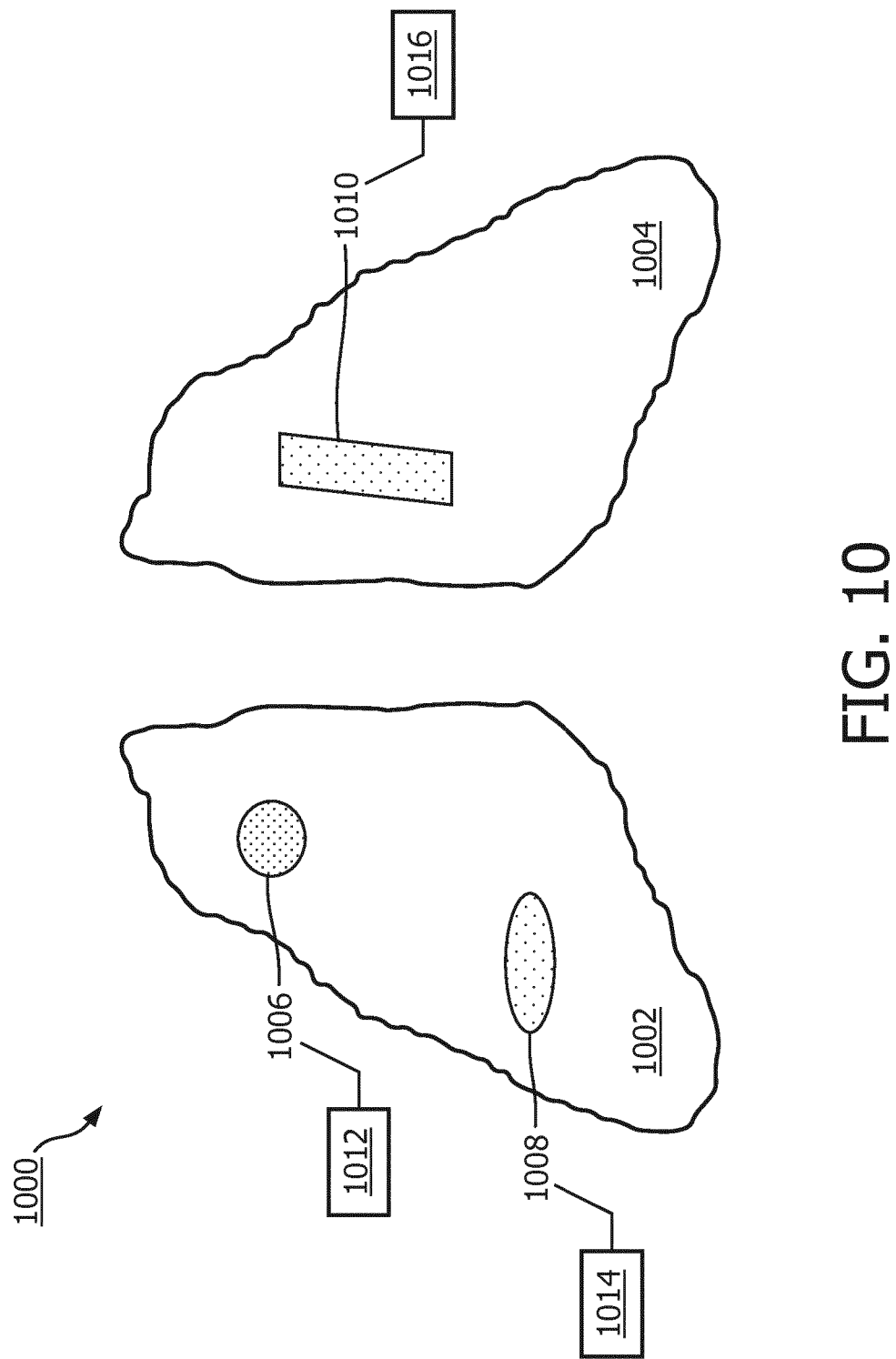
FIG. 10 is a graphic generated and displayed on a user interface for guiding a user through an ultrasound scan of a pulmonary region.

As mentioned above, a user interface disclosed herein, in cooperation with one or more processors, e.g., data processor 126, signal processor 122 and/or display processor 128, can be configured to provide instructions or information effective to guide a user through an ultrasound scan, thereby detecting lung abnormalities, such as lung consolidations. FIG. 10 shows an example of a graphic 1000 that may be generated and displayed on a user interface, such as user interface 130. The graphic 1000 comprises a chest region of the patient being scanned, showing both lungs 1002, 1004. Within the lungs, the graphic 1000 includes abnormality indicators 1006, 1008, 1010 superimposed over abnormality locations that were determined through one or more previously performed ultrasound scans. By aligning an ultrasound probe with the locations 1006, 1008, 1010 provided on the graphic 1000, a user can obtain image frames of the previously identified lung abnormalities. Upon detection of new abnormalities, the graphic can be updated to include new indicators at the correct anatomical locations. The indicators 1006, 1008, 1010 may also be labeled in terms of the severity of an abnormality. For example, an indicator may be color-coded red if the underlying abnormality is particularly large or fast-growing, while the indicator may be color-coded blue if the underlying abnormality is relatively minor or slowly-changing, or even decreasing in size, thus providing an indication of treatment effectiveness. In some examples, each indicator may correspond to the size, shape and/or type of the underlying abnormality. For example, one or more processors herein may be configured to generate, in cooperation with the user interface, larger indicators to designate larger abnormalities, and vice-versa.

In some embodiments, the indicators 1006, 10008, 1010 can be displayed concurrently with user instructions 1012, 1014, 1016 for positioning and/or orienting the ultrasound probe in the manner necessary to image the underlying abnormalities. In various examples, an instruction may include at least a probe angle with respect to the surface of the patient and an orientation. Instructions may also include the probe settings used to detect or monitor an abnormality during at least one previous scan. In some embodiments, the instructions may be accompanied by general information about a lung abnormality, e.g., volume, volume change rate, depth, severity, etc.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods. Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

The invention claimed is:

1. An ultrasound imaging system comprising:
   an ultrasound transducer configured to acquire echoes responsive to ultrasound pulses transmitted toward a target region comprising a lung;
   a processor in communication with the ultrasound transducer and configured to:
   generate an image frame from the echoes, wherein each pixel in the image frame corresponds to a different spatial point in the target region and the image frame is a B-mode ultrasound image;
   determine a uniformity characteristic of a region of interest below a pleural line in the image frame;
   determine a presence or absence of a lung abnormality within the region of interest based on a value of the uniformity characteristic, wherein the uniformity characteristic comprises a standard deviation from an average image intensity;
   generate and update an indicator, concurrently to the echoes being acquired, if the lung abnormality has been determined to be present in the image frame; and
   display the indicator on a user interface in communication with the processor.

2. The ultrasound imaging system of claim 1, wherein the processor is configured to quantify the uniformity characteristic in the form of a spatial correlation map of image intensity.

3. The ultrasound imaging system of claim 2, wherein the processor is configured to determine the spatial correlation map.

4. The ultrasound imaging system of claim 3, wherein the processor is configured to adjust the defined interval of pixels in response to a user input received at the user interface.

5. The ultrasound imaging system of claim 1, wherein the uniformity characteristic further comprises a total speckle size within the region of interest.

6. The ultrasound imaging system of claim 1, wherein the lung abnormality is lung consolidation, and wherein the processor is further configured to apply a threshold value to the uniformity characteristic, wherein the presence of a lung consolidation is confirmed if the value of the uniformity characteristic exceeds the threshold value.

7. The ultrasound imaging system of claim 1, wherein the user interface is further configured to display a number of lung abnormalities present within the region of interest, a location of the lung abnormality, a type of the lung abnormality, a variation in lung abnormality volume, or combinations thereof.

8. The ultrasound imaging system of claim 1, wherein the user interface is configured to generate and display an ultrasound image during an ultrasound scan, wherein the indicator comprises a graphic overlay superimposed on the lung abnormality within the ultrasound image.

9. The ultrasound imaging system of claim 1, wherein the user interface is further configured to guide a user through an ultrasound scan of the target region of a patient by providing an instruction for orienting the ultrasound transducer.

10. The ultrasound imaging system of claim 9, wherein the instruction is based on a previously conducted ultrasound scan of the patient and stored in a memory coupled with the processor.

11. A method of ultrasound imaging, the method comprising:
   acquiring echo signals responsive to ultrasound pulses transmitted into a target region comprising a lung by a transducer operatively coupled to an ultrasound system;
   generating an image frame from the ultrasound echoes, wherein each pixel in the image frame corresponds to a different spatial point in the target region and the image frame is a B-mode ultrasound image;
      determining a uniformity characteristic of a region of interest below a pleural line in the image frame;
   determining a presence or absence of a lung abnormality within the region of interest based on a value of the uniformity characteristic, wherein the uniformity characteristic comprises a standard deviation from an average image intensity;
   generating and updating an indicator, concurrently to the echoes being acquired, if the lung abnormality has been determined to be present in the image frame; and
   displaying the indicator on a user interface in communication with a processor.

12. The method of claim 11, further comprising quantifying the uniformity characteristic in the form of a spatial correlation map of image intensity.

13. The method of claim 12, wherein the spatial correlation is determined by comparing image intensity values of pairs of individual pixels within the image frame, the pairs laterally separated by a defined interval of pixels.

14. The method of claim 11, further comprising at least one of:
   generating a report comprising a number of lung abnormalities present within the region of interest, a location of the lung abnormality, a type of the lung abnormality, a variation in lung abnormality volume, or combinations thereof;
   guiding a user through an ultrasound scan of the target region of a patient by providing an instruction for orienting the transducer; and
   determining a scan distance to the lung abnormality during the ultrasound scan.

15. A non-transitory computer-readable medium comprising executable instructions, which when executed cause a processor of an ultrasound imaging system to;
   acquire echo signals responsive to ultrasound pulses transmitted into a target region comprising a lung by a transducer operatively coupled to an ultrasound system;
   generate an image frame from the ultrasound echoes, wherein each pixel in the image frame corresponds to a different spatial point in the target region and the image frame is a B-mode ultrasound image;
   determine a uniformity characteristic of a region of interest below a pleural line in the image frame;
   determine a presence or absence of a lung abnormality within the region of interest based on a value of the uniformity characteristic, wherein the uniformity characteristic comprises a standard deviation from an average image intensity;
   generate and update an indicator, concurrently to the echoes being acquired, if the lung abnormality has been determined to be present in the image frame; and
   display the indicator on a user interface in communication with a processor.

16. A non-transitory computer-readable medium comprising executable instructions, which when executed cause a processor of an ultrasound system to:
   receive an image frame, the image frame being generated from ultrasound echo data acquired from a target region comprising a lung, wherein each pixel in the image frame corresponds to a different spatial point in the target region and the image frame is a B-mode ultrasound image;
   determine a uniformity characteristic of a region of interest below a pleural line in the image frame;
   determine a presence or absence of a lung abnormality within the region of interest based on a value of the uniformity characteristic, wherein the uniformity characteristic comprises a standard deviation from an average image intensity; and
   generate and update an indicator, concurrently to the echoes being acquired, if the lung abnormality has been determined to be present in the image frame.

17. An apparatus for detecting lung abnormality on basis of ultrasound echo data, comprising:
   a data interface configured to:
   receive an image frame, the image frame being generated from ultrasound echo data acquired from a target region comprising a lung, wherein each pixel in the image frame corresponds to a different spatial point in the target region and the image frame is a B-mode ultrasound image; and
   output an indicator if a lung abnormality has been determined to be present; and
   a processor configured to:
   determine a uniformity characteristic of a region of interest below a pleural line in the image frame;
   determine a presence or absence of the lung abnormality within the region of interest based on a value of the uniformity characteristic, wherein the uniformity characteristic comprises a standard deviation from an average image intensity; and
   generate and updating the indicator, concurrently to the echoes being acquired, if the lung abnormality has been determined to be present in the image frame.

* * * * *